US011701165B2

United States Patent
Marion et al.

(10) Patent No.: US 11,701,165 B2
(45) Date of Patent: Jul. 18, 2023

(54) SYSTEM AND METHOD TO PROTECT AGAINST INSULATION BREACH IN AN ELECTROSURGICAL INSTRUMENT

(71) Applicant: Intuitive Surgical Operations, Inc., Sunnyvale, CA (US)

(72) Inventors: Duane W. Marion, Scottsdale, AZ (US); Thomas G. Cooper, Menlo Park, CA (US); Eric J. Earnst, Saratoga, CA (US); Jason W. Hemphill, Los Gatos, CA (US); Alan E. Loh, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 847 days.

(21) Appl. No.: 16/616,711

(22) PCT Filed: May 31, 2018

(86) PCT No.: PCT/US2018/035436
§ 371 (c)(1),
(2) Date: Nov. 25, 2019

(87) PCT Pub. No.: WO2018/222899
PCT Pub. Date: Dec. 6, 2018

(65) Prior Publication Data
US 2021/0145504 A1    May 20, 2021

Related U.S. Application Data

(60) Provisional application No. 62/513,282, filed on May 31, 2017.

(51) Int. Cl.
*A61B 18/12* (2006.01)
*A61B 18/16* (2006.01)
*A61B 18/00* (2006.01)

(52) U.S. Cl.
CPC .......... *A61B 18/1233* (2013.01); *A61B 18/16* (2013.01); *A61B 2018/00077* (2013.01);
(Continued)

(58) Field of Classification Search
CPC ..... A61B 18/1233; A61B 18/14; A61B 18/16; A61B 2018/00077; A61B 2018/00083;
(Continued)

(56) References Cited

U.S. PATENT DOCUMENTS 4,416,277 A   11/1983   Newton et al.
4,602,308 A   7/1986   Montague
(Continued)

FOREIGN PATENT DOCUMENTS

CN   105592886 A   5/2016

OTHER PUBLICATIONS

International Preliminary Report on Patentability for Application No. PCT/US2018/035436, dated Dec. 12, 2019, 8 pages.
(Continued)

*Primary Examiner* — Khadijeh A Vahdat
(74) *Attorney, Agent, or Firm* — Schwegman, Lundberg & Woessner, P.A.

(57) ABSTRACT

An apparatus is provided to detect electrical contact between anatomical tissue and a shield conductor: a transformer; an alternating current (AC) reference frequency signal generator to inject a reference frequency signal to a primary winding of the transformer; a reactive impedance coupled in parallel with a secondary winding of the transformer between a first node and a second node; and a phase match detector circuit to detect a phase match between the reference frequency signal and a reflected reference frequency signal that is reflected from the secondary winding to the primary winding.

18 Claims, 7 Drawing Sheets

(52) U.S. Cl.
CPC ........... *A61B 2018/00083* (2013.01); *A61B 2018/00845* (2013.01); *A61B 2018/00869* (2013.01); *A61B 2018/00875* (2013.01); *A61B 2018/00892* (2013.01); *A61B 2018/00904* (2013.01); *A61B 2018/1286* (2013.01); *A61B 2018/167* (2013.01)

(58) Field of Classification Search
CPC .......... A61B 2018/00577; A61B 2018/00601; A61B 2018/00827; A61B 2018/00845; A61B 2018/00869; A61B 2018/00875; A61B 2018/00892; A61B 2018/00904; A61B 2018/1253; A61B 2018/1286; A61B 2018/1422; A61B 2018/1425; A61B 2018/1432; A61B 2018/167
See application file for complete search history.

(56) References Cited

U.S. PATENT DOCUMENTS

| | | |
|---|---|---|
| 4,896,115 A | 1/1990 | LeMaitre et al. |
| 6,464,696 B1 | 10/2002 | Oyama et al. |
| 6,565,558 B1 | 5/2003 | Lindenmeier et al. |
| 2009/0234353 A1 | 9/2009 | McPherson |
| 2015/0171728 A1 | 6/2015 | Gong et al. |
| 2015/0359584 A1 | 12/2015 | Newton |

OTHER PUBLICATIONS

Extended European Search Report for Application No. EP18809136.7 dated Feb. 3, 2021, 07 pages.

International Search Report and Written Opinion for Application No. PCT/US2018/035436, dated Sep. 27, 2018, 11 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

SYSTEM AND METHOD TO PROTECT AGAINST INSULATION BREACH IN AN ELECTROSURGICAL INSTRUMENT

CLAIM OF PRIORITY

This application is a U.S. National Stage Filing under 35 U.S.C. 371 from International Application No. PCT/US2018/035436, filed on May 31, 2018, and published as WO 2018/222899 A1 on Dec. 6, 2018, which claims the benefit of priority to U.S. Provisional Patent Application No. 62/513,282, filed on May 31, 2017, each of which is herein incorporated by reference herein in its entirety.

BACKGROUND

Electrosurgery involves the use of electricity to cause thermal destruction of biological tissue to cut or remove the tissue through desiccation, coagulation, or vaporization, for example. Benefits include the ability to make precise cuts with limited blood loss. Electrosurgical instruments are frequently used during surgical procedures to help prevent blood loss in hospital operating rooms or in outpatient procedures. The two types of electrosurgery most commonly used are high-frequency electrosurgery and electrocautery. High-frequency electrosurgery involves high-frequency (radio frequency) alternating current that is converted to heat by resistance as it passes through the tissue. The heat buildup within the tissue causes thermal tissue damage resulting in incision or debulking, for example. Electrocautery also involves direct transference of heat to tissue. Instead of passing electrical current through the tissue, however, the current is used to heat a handheld element, which is then applied to the tissue. Additional modalities of electrosurgery include electrolysis, which uses a chemical reaction created by direct current to damage tissue, and coblation, which uses an electrical current to ionize a conduction medium such as isotonic saline, which is then used to transmit heat to tissue.

FIG. 1 is an illustrative partially cut-away cross-sectional side elevation view of an elongated tubular instrument shaft 102 enclosing an active electrode 104 of an electrosurgical instrument. The shaft 102 includes an elongated tubular safety shield conductor (shield) 106 that is surrounded by a non-conducting tubular outer insulating sheath 108. The shield 106 surrounds the active conductor 104, also referred to as an active electrode, to provide protection against unintended parasitic capacitive coupling of electrosurgical energy from active electrode 104 to metallic objects adjacent to instrument shaft 102. A high dielectric insulator 110 is disposed between the shield 106 and the active electrode 104.

FIG. 2 is an illustrative system level block diagram representing setup of a first monopolar electrosurgical system 200. The system 200 includes a monopolar electrosurgical signal generator 202, which delivers a high frequency electrical signal on the active conductor 104 of an electrosurgical instrument (ESI) 203. A patient's biological tissue 204 is electrically coupled between the active conductor 104 and a return conductor 205. During a surgical procedure, the active conductor 104 contacts a tissue portion 206 at a surgical site at which tissue is to be cut or ablated, for example. Electrosurgical instrument (ESI) current flows from the active conductor 104 to the patient tissue portion 206 at the surgical site and from there, to another patient tissue portion 208 that contacts a patient return conductor pad 210. The ESI current flows from the return conductor pad 210 to the return conductor 205. More particularly, an end effector tip portion 212 of the active conductor 104 extends beyond the end of the shaft 102 to impart energy at the surgery location to cut or remove biological tissue. Thus, ESI current flows from the active conductor tip 212, to the patient tissue portion 206 at a surgical location, through patient anatomy 204, to the patient tissue portion 208 at the return pad, and through the generator's return conductor 205 to the generator 202.

FIG. 3A is an illustrative block diagram representing setup of a second electrosurgical system 300. The second electrosurgical system 300 includes a monopolar electrosurgical signal generator 202 and a first monitor circuit 304. Components of the second system 300 that may be identical to those of the first system 200 are identified with the identical reference numerals and will be understood from the above description. A protective conductor 306 that couples a protective impedance $Z_P$ between the safety shield conductor 106 and the return conductor 205 provides a protective current path between them. FIG. 3B is an illustrative cross-sectional side elevation view of a portion of the instrument shaft 102 showing an electrical contact 303 between the shield conductor 106 and the protective electrical conductor 306. The protective impedance $Z_P$ includes resistive and reactive elements, such as capacitive, (not shown) that couple the shield conductor 106 and the return conductor 205 to limit the high frequency energy that can be delivered from the safety shield conductor 106 to other instruments (not shown), for example. Capacitively coupled energy may potentially lead to electrical arcing or conduction to patient tissue 204 that may cause thermal injury to patient tissue 204. For this protection to be maintained, the shield conductor must be electrically isolated from the patient tissue. If the insulation sheath 108 surrounding the shield conductor 106 is damaged and the underlying shield conductor 106 contacts patient tissue 204, then the electrical conductor 306 and the protective impedance $Z_P$ may provide a conductive path for aberrant ESI current flow from the active conductor tip 212, through patient tissue 204, to the safety shield conductor 106, and then to the return conductor 205 via the electrical conductor 306 and the protective impedance $Z_P$ resulting in a thermal injury to patient tissue 204.

FIGS. 4A-4B are illustrative drawings of a portion of the second system 300 of FIG. 3A representing normal ESI current ($I_{ESI}$) path 410 through patient tissue 204 during a surgical procedure during normal operation (FIG. 4A) and representing aberrant ESI current path 412 through patient tissue 204 during operation with a breach in the insulation sheath 108 surrounding the conductor safety shield (106 is also called "shield conductor") 106 (FIG. 4B). During normal operation, represented by FIG. 4A, ESI current flows from the active conductor tip 212 to the return pad 210. The return pad 210 has a surface area that is large enough so that patient tissue 208 in physical contact with the pad has a large enough surface area so that the return ESI current spreads across a wide enough patient tissue area to limit the current density sufficiently to avoid tissue burns or other trauma due to the return ESI current, for example. As represented in FIG. 4B, a breach 414 in the insulation 108 may occur, for example, due to another instrument (not shown) physically contacting the shaft 102 during a surgical procedure. The insulation layer 108 may in some cases be damaged because of unintended or aggressive use during the surgical procedure. The aberrant ESI current 412 may flow from the active conductor tip 212, which may contact the patient tissue portion 206 at a surgical site, to another patient tissue portion 402 that physically contacts an exposed portion 404 of the safety shield conductor 104 that is exposed to physical contact with the patient tissue portion due to a breach in the insulation layer 108. Since an insulation breach dimension typically is small, much smaller than the dimensions of the contact pad 210, the current density at the breach portion 404 of the safety shield conductor 104 may be larger than that at the contact pad 210, creating a risk of thermal injury to the patient at the tissue portion 402 in contact with the shield conductor 106 due to the aberrant ESI current flow 412 from the active electrode tip 212, through patient tissue portion 402, to the exposed portion 404 of the shield conductor 106.

Referring to FIG. 3A and FIG. 4B, the first monitor circuit 304 preferably deactivates the electrosurgical signal generator 202 in response to current on the protective conductor current path 306 exceeding a threshold level due to an abnormal condition such as aberrant current flow 412 due to a breach 414 in the insulation 108 that exposes a portion of the shield conductor 106 to contact patient tissue 204, for example. Example monitor circuits are described in U.S. Pat. Nos. 4,414,277; 5,312,401; and 8,007,494; and in US Pub No. 2014/0249523. A problem with monitoring current flow within a conductor 306 coupled to a protective impedance $Z_P$ to determine when to deactivate an electrosurgical signal generator 202 due to aberrant ESI current 412 is that there may be some desirable level of current passed through the conductor 306 to suppress a parasitic capacitance between the active conductor 104 and other instruments, for example. However, the magnitude of desired current flow to reduce parasitic capacitance may vary depending upon the generator settings and the instrument design, for example. Therefore, it may be difficult to select an appropriate threshold current that can allow for this intended current delivery, which may vary, and still provide an adequate margin of safety against aberrant ESI current 412 that may cause thermal injury in the event insulation breach, for example.

SUMMARY

In one aspect, a phase difference between an alternating current (AC) reference signal injected to a primary winding of a transformer and a reflected AC frequency reflected from a secondary winding of the transformer to the primary winding is used to determine whether or not an electrical path exists between a safety shield conductor surrounding an active electrode of an electrosurgical instrument and patient tissue.

DESCRIPTION OF EMBODIMENTS

Figure 1:
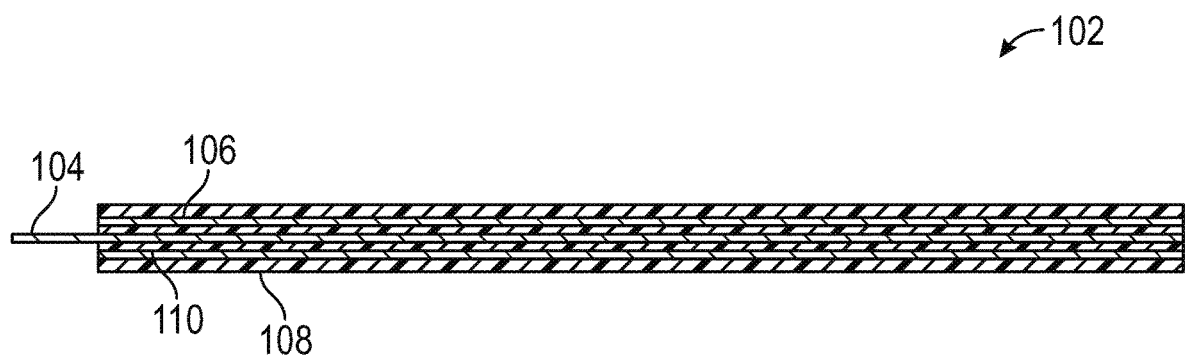
FIG. 1 is an illustrative partially cut-away side elevation view of an elongated tubular instrument shaft enclosing an active electrode of an electrosurgical instrument.
Figure 2:
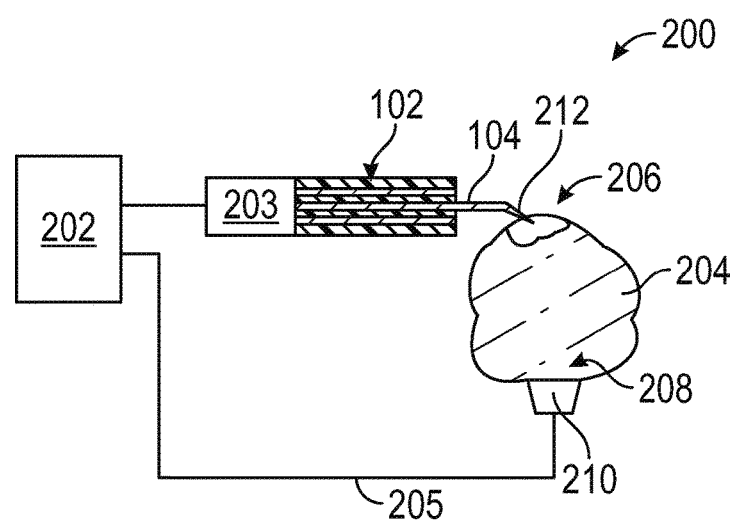
FIG. 2 is an illustrative system level block diagram representing setup of a first electrosurgical system.
Figure 3B:
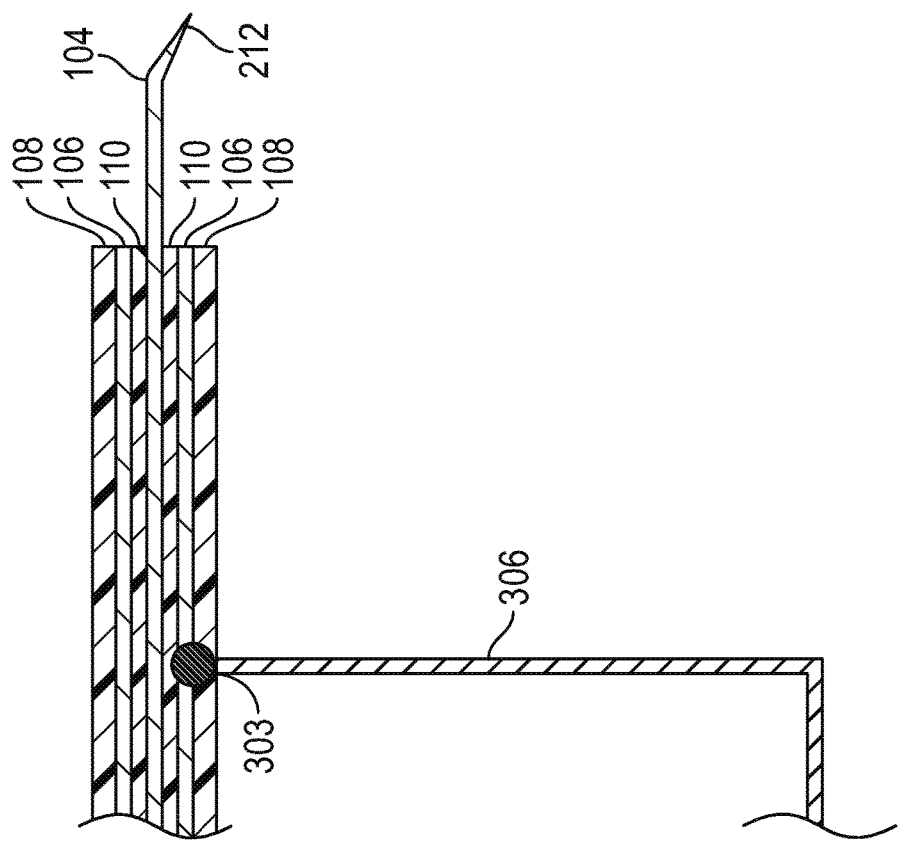
FIG. 3B is an illustrative cross-sectional side elevation view of a portion of the instrument shaft of the system of FIG. 3A showing an electrical contact between the shield conductor and an electrical conductor coupled to a protective impedance.
Figure 3A:
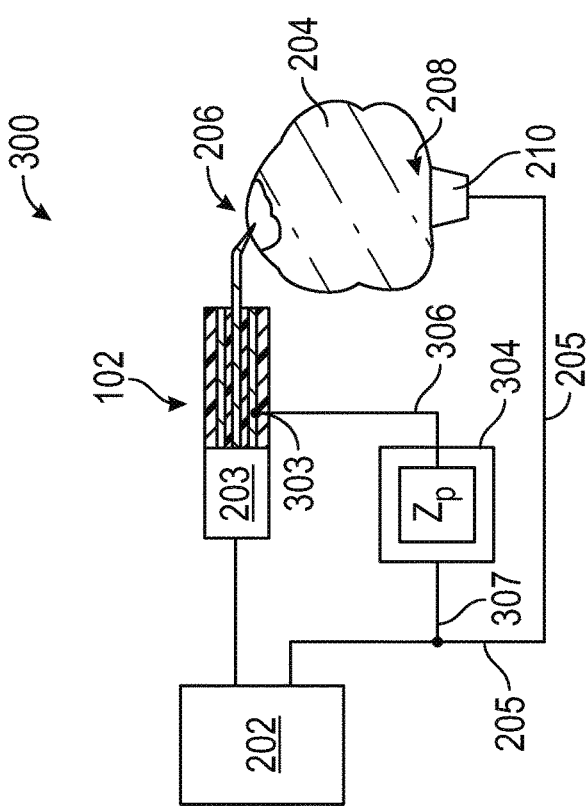
FIG. 3A is an illustrative block diagram representing setup of a second electrosurgical system that includes a first monitor circuit.
Figure 4A:
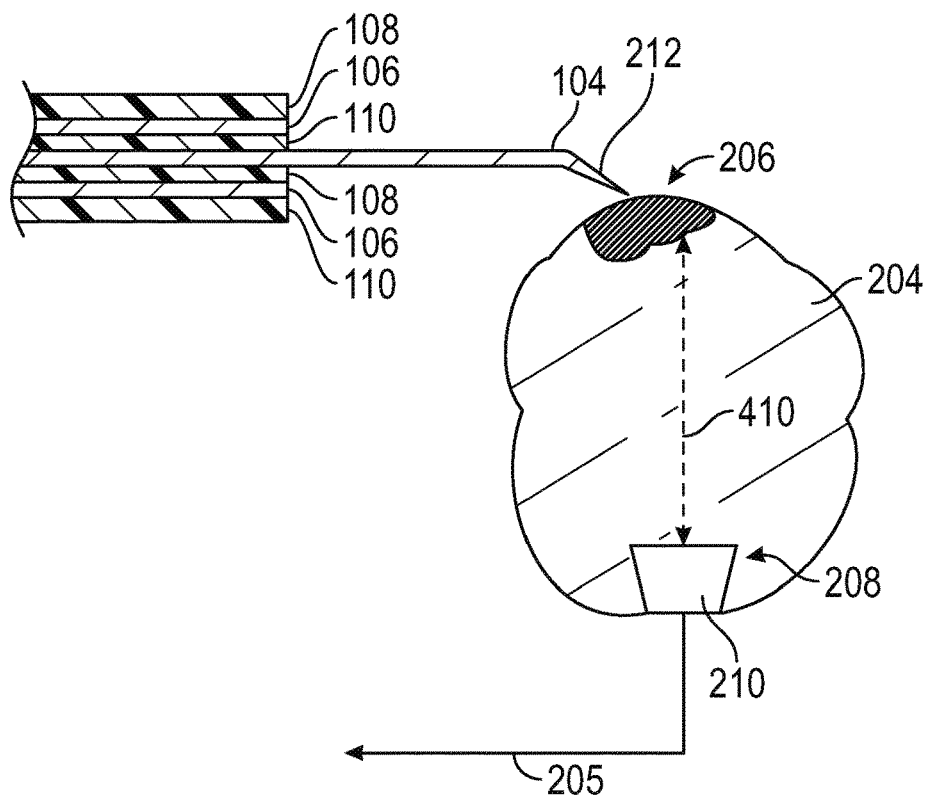
FIGS. 4A-4B are illustrative drawings of a portion of the second system of FIGS. 3A-3B showing electrosurgical instrument current flow through patient tissue during a surgical procedure during normal operation (FIG. 4A) and during operation with a breach in the insulation sheath surrounding the conductor safety shield (FIG. 4B).
Figure 4B:
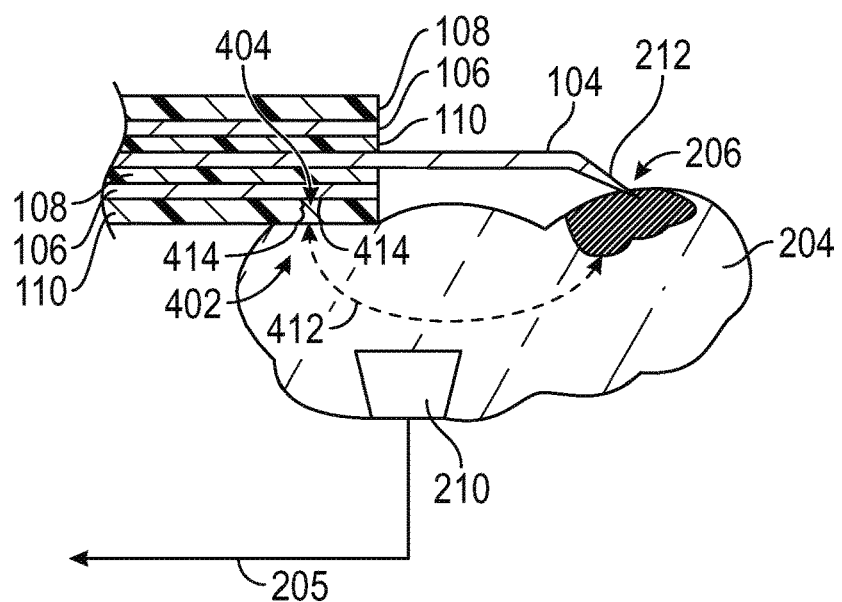
Figure 5A:
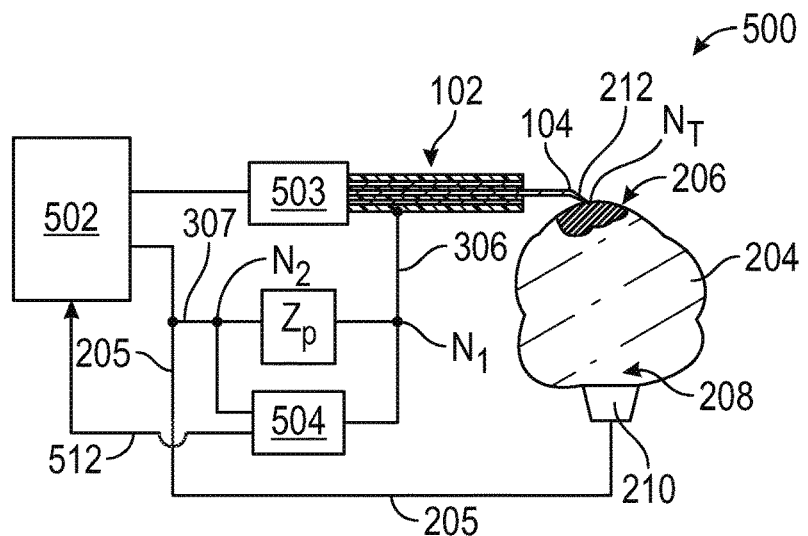
FIG. 5A is an illustrative schematic diagram representing setup of a third electrosurgical system.

FIG. 5A is an illustrative schematic diagram representing setup of a third electrosurgical system 500. The third system 500 includes a monopolar electrosurgical signal generator 502 and a second monitor circuit 504. The electrosurgical signal generator 502 produces a high frequency ESI current to an active conductor 104 for use in electrosurgery. In some embodiments, the generator produces a 3 kV, 350 kHz signal. The active conductor 104 extends within an elongated shaft 102. An end effector tip 212 of the active conductor 104 extends beyond a distal end of the shaft 102 to impart energy to cut or remove patient's tissue 204 at a surgery location adjacent 206 to or in contact with the tip. The end effector tip 212 may be of various shapes such as needle-shape, hook-shape, spatula-shape, graspers, scissors, for example. During normal operation, high frequency ESI current flows between a proximal end of the shaft 102 adjacent the signal generator 502 and a distal end tip 212 of the shaft 102 adjacent to a patient tissue portion 206 at a surgical site. A patient return pad 210 physically contacts a patient tissue portion 208 at a location on the patient's tissue 204 that is outside of the surgical region. A return conductor 205 couples the return pad 210 to a return node of the signal generator 502. A protective conductor path includes a protective impedance $Z_P$ coupled between a safety shield conductor 106 and the return conductor 205. More particularly, first and second protective path conductors 306, 307 couple the protective impedance $Z_P$ between first and second nodes $N_1$, $N_2$. The first conductor 306 couples the first node $N_1$ to the protective shield conductor 106. The second conductor 307 couples the second node $N_2$ to the return path 205. During normal operation, normal ESI current 410 may flow from the active electrode tip 212, to patient tissue portion 206 at the surgical location, through patient tissue anatomy 204, to patient tissue 208 at the patient return pad 210, and then, through the return conductor 205 to the signal generator's return node, for example. The protective impedance $Z_P$ includes resistive and reactive elements (not shown) to limit potential inadvertent energy delivery due to capacitive coupling between the shield conductor 106 and other instruments (not shown) during normal operation i.e. in the absence of an insulation breach, for example.

Figure 5B:
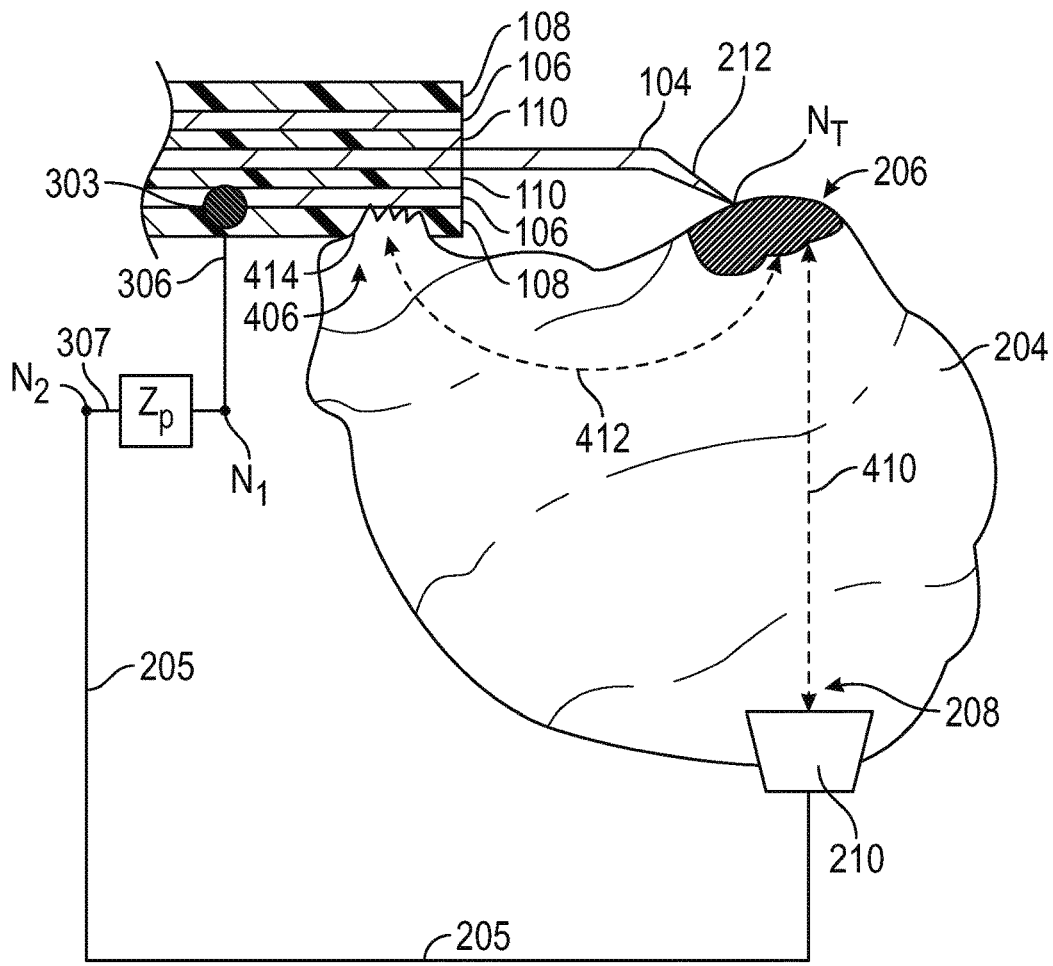
FIG. 5B is an illustrative drawing showing portions of the third system of FIG. 5A to illustrate current paths during normal and aberrant ESI current flow.

FIG. 5B is an illustrative drawing showing portions of the third system 500 of FIG. 5A to illustrate current paths during normal and aberrant ESI current flow. In operation, if a breach 414 occurs in the protective insulation layer 108 due to damage, for example, then unwanted electrical contact between a patient tissue portion 406 and an exposed portion of the conductor shield 106, may create a potentially harmful, aberrant current path 412 between patient tissue at a surgical site 206 and patient tissue 406 in contact with a portion of the conductive shield 106 exposed due to the breach in the insulation layer 108. Moreover, the aberrant circuit path may include the protective current path formed by conductor 306 the protective impedance $Z_P$ and the second conductor 307, which is coupled to the return lead 205. Aberrant ESI current flow 412 may pose a risk of thermal injury to a patient, for example.

Figure 5C:
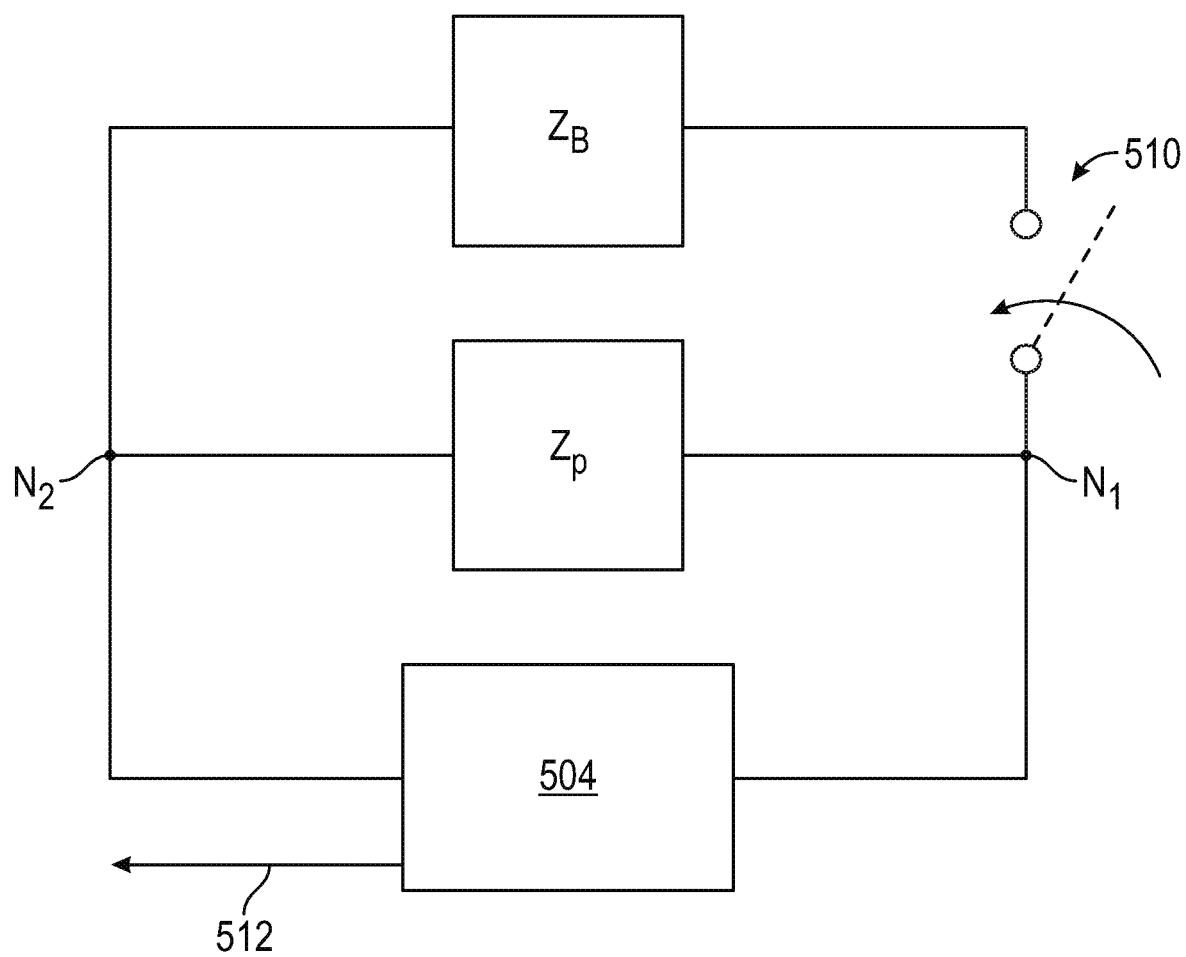
FIG. 5C is an illustrative circuit diagram representing parallel coupling of protective impedance and body impedance during normal and aberrant ESI current flow.

During normal ESI current flow, patient tissue 204 is not coupled in parallel with the protective impedance $Z_P$ between a node the first and second nodes $N_1$, $N_2$. However, during aberrant ESI current flow, patient tissue 204 is coupled in parallel with the protective impedance $Z_P$ between a node the first and second nodes $N_1$, $N_2$. Thus, parallel coupling of patient tissue 204 during aberrant current flow results in a patient body tissue impedance $Z_B$ coupled in parallel with the protective impedance $Z_P$. More particularly, normal ESI current path 410 includes patient tissue 204 between a node $N_T$ where the tip 212 contacts patient tissue 206 in the surgical region and the patient contact pad 210, which is electrically coupled via return conductor 205 and the second conductor 307 to the second node $N_2$. During normal ESI current flow, there is no electrical coupling between the patient tissue 204 and the shield conductor 106 or the first node $N_1$. However, during aberrant ESI current flow due to tissue contact with a shield conductor 106 resulting from a breach 414 in the insulation sheath 108, for example, patient tissue 204 is coupled in an electrical path that includes the normal electrical path 410, and that also includes a path that extends between the node $N_T$ where the active conductor tip 212 contacts the patent tissue 206, a patient tissue portion 406 in contact with the shield 106, the first conductor 306 and the first node $N_1$. Thus, impedance across the first and second nodes $N_1$, $N_2$ changes in response to inclusion of patient tissue 204 in contact with the shield conductor 106 due to a breach in the insulative shield 108. FIG. 5C is an illustrative circuit diagram showing portions of the third system 500 to illustrate parallel coupling of the protective impedance $Z_P$ and the body impedance $Z_B$ within the third system of FIGS. 5A-5B. A virtual switch 510 in an open position represents operation of the system 500 with no breach in the insulation sheath 108 when the body impedance $Z_B$ is not coupled in parallel with the protective impedance $Z_P$ during normal ESI current flow. The virtual switch 510 in a closed position represents operation of the system 500 with a breach 414 in the insulation sheath 108 resulting in coupling of the body impedance $Z_B$ in parallel with the protective impedance $Z_P$ during aberrant ESI current flow. The second monitor circuit 504 monitors impedance between nodes the first and second nodes $N_1$, $N_2$ to detect an occurrence of a change impedance between them. The second monitor circuit 504 provides a detector control signal on an output node 512 that is coupled to cause the electrosurgical signal generator 502 system to transition to block ESI current flow to the active conductor tip 212 in response to detection of a change in impedance $Z_P$ that indicates coupling of the body impedance $Z_B$ in parallel with the protective $Z_P$.

Figure 6:
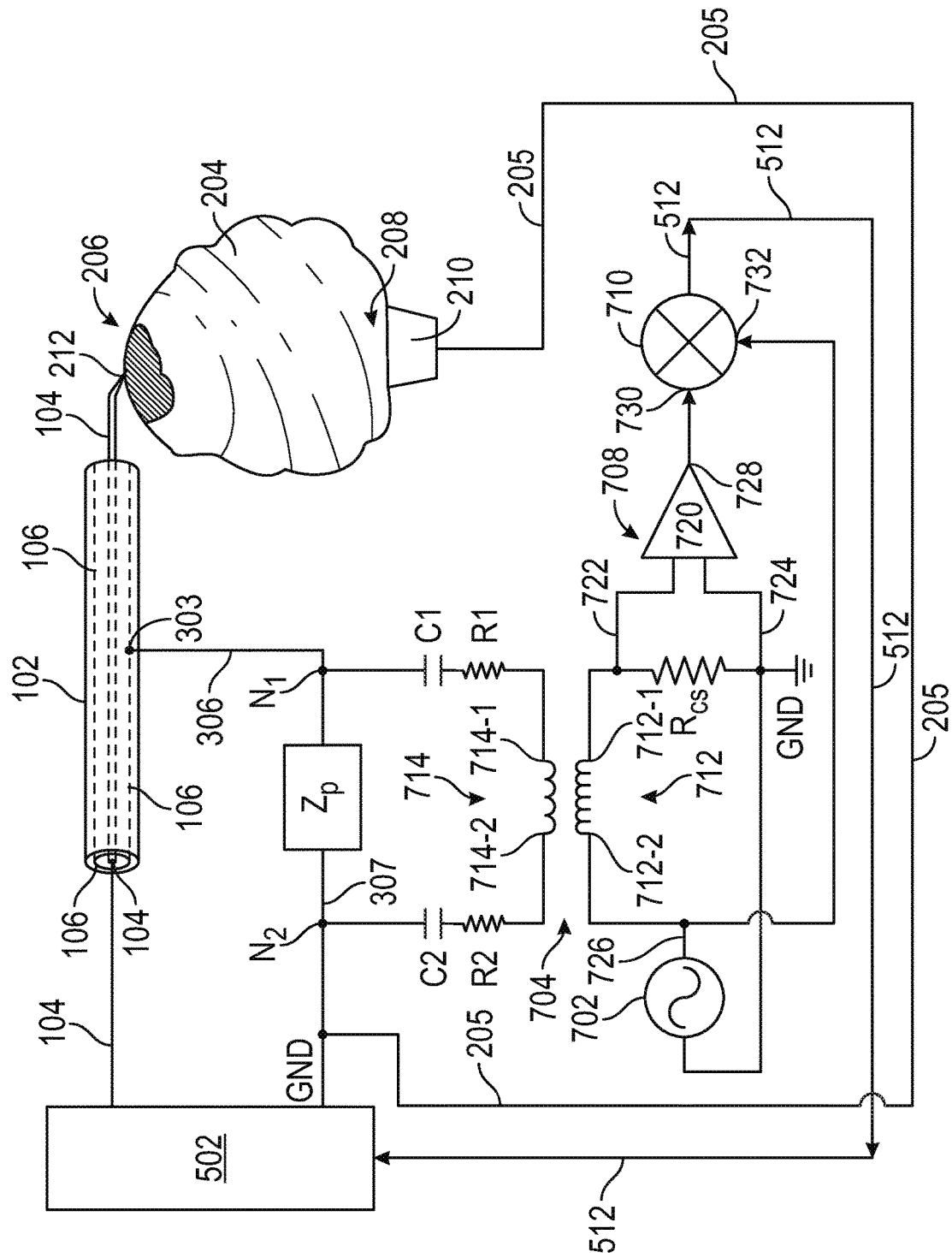
FIG. 6 is an illustrative drawing of the third system of FIG. 5A showing additional details of the second monitor circuit.

FIG. 6 is an illustrative drawing of the third system of FIG. 5A showing additional details of the second monitor circuit 504. The second monitor circuit 504 includes an alternating current (AC) reference signal generator 702, a transformer 704, a current sensing circuit 708 and a phase match detector 710. The AC reference signal generator 702 produces a reference signal at a reference signal frequency that is distinguishable from a frequency of an ESI signal produced by the electrosurgical signal generator 502. In some embodiments, the reference signal has a reference signal frequency of 45 kHz. The transformer 704 includes a primary winding 712 and a secondary winding 714. The protective impedance $Z_P$ is coupled between a first node $N_1$ and a second node $N_2$. A first capacitance C1 and a first resistance R1 are coupled in series between the first node $N_1$ and a first end 714-1 of the secondary winding 714. A second capacitance C2 and a second resistance R2 are coupled in series between the second node $N_2$ and a second end 714-2 of the secondary winding 714. The values of these components are selected to provide the intended amount of discrimination between the frequency of the reference signal and the fundamental frequency of the ESI signal.

The current sensing circuit 708 includes a differential amplifier circuit 720 that includes a first input 722 and a first input 724. A current sensing resistor $R_{CS}$ is coupled between the first and second inputs 722, 724 of the differential amplifier circuit 720. More particularly, the first input 722 of the differential amplifier circuit 720 is coupled between a first node of the current sense resistor $R_{CS}$ and a first end 712-1 of the primary winding 712, and the second input 724 of the differential amplifier circuit 720 is coupled between a second terminal node of the current sense resistor $R_{CS}$ and a reference potential 724, which may be ground potential. An output 728 of the current sensing circuit 708 is coupled to a first input 730 of the phase match detector 710. The AC reference signal generator 702 includes an AC reference signal output 726 coupled to a second end 712-2 of the primary winding 712. The AC reference signal node 726 also is coupled to a second input 732 of the phase match detector 710. The phase match detector 710 includes the output 512 to provide the detector control signal that has a value to indicate whether a body impedance $Z_B$ is coupled in parallel with the protective impedance $Z_P$ between the first and second nodes $N_1$, $N_2$.

Figure 7:
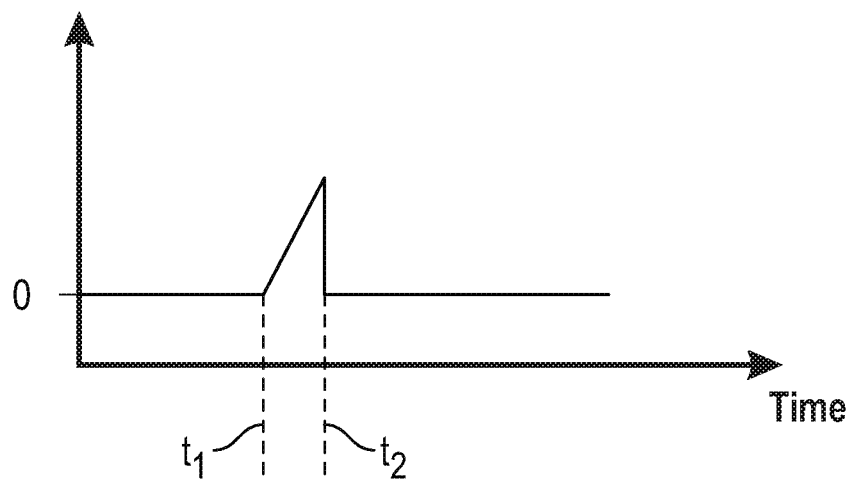
FIG. 7 is an illustrative example aberrant ESI signal timing diagram.

FIG. 7 is an illustrative example aberrant ESI signal timing diagram. During a first example time interval, t0 to t1, no aberrant ESI current flows between the safety shield conductor 106 and the return lead 205. During a second time interval, t1 to t2, aberrant ESI current flows between the safety shield conductor 106 and the return lead 205.

Figure 8:
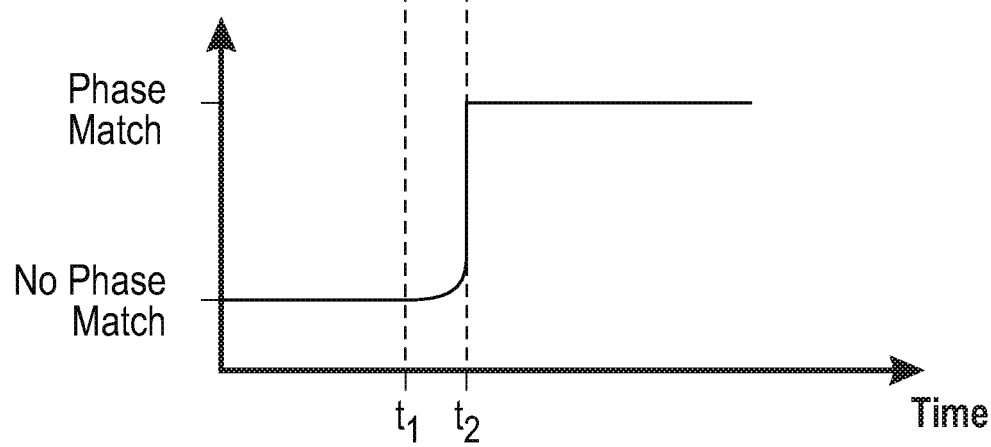
FIG. 8 is an illustrative example detector control signal timing diagram.

FIG. 8 is an illustrative example detector control signal timing diagram. During the first example time interval, t0 to t1, the detector control signal on line 512 has a first value to indicate that no phase match indicative of no aberrant ESI current flows between the safety shield conductor 106 and the return lead 205. During a second time interval beginning at time, t2, the detector control signal on line 512 has a value to indicate a phase match indicative of aberrant ESI current flows between the safety shield conductor 106 and the return lead 205. Referring again to FIG. 7, it will be understood that the electrosurgical signal generator 502 turns off in response to the control signal transitioning to the second value at time t2 resulting in halting of the aberrant ESI current flow.

Operation of the third electrosurgical system 500 that includes the second monitor circuit 504 of FIGS. 5-6 is explained with reference to the signal timing diagrams of FIGS. 7-8. The AC reference signal generator 702 is coupled to inject an reference frequency signal at its output 726 to the primary winding. The injected reference frequency signal is magnetically coupled from the primary winding 712 to the secondary winding 714. The coupled AC reference signal flows through the protective impedance $Z_P$, which is coupled between the first and second nodes $N_1$, $N_2$. The capacitance C1 and first resistance R1 and the second capacitance C2 and a second resistance R2 act as low pass filters that are intended to filter out signals with frequencies above that of the AC reference signal. An AC reference frequency current that flows through the protective impedance $Z_P$ reflects back from the secondary winding 714 to the primary winding 712. The reflected AC reference frequency current flows through current sense resistor $R_{CS}$. The differential amplifier 720 produces an AC voltage value at its output 728 that is indicative of AC voltage drop across the current sense resistor $R_{CS}$ due to the reflected AC reference frequency current.

The phase match detector 710 produces the control signal on control line 512 in response to an indication of the reflected AC reference frequency signal provided on its first input 730 and the AC reference frequency signal received at its second input 732. In some embodiments, the phase match detector 710 produces a DC control signal on line 512 having a value indicative of the phase and frequency relationship of the AC voltage signal received at its first input 730, which is indicative of the reflected AC reference frequency signal, and the AC reference signal received at its second input 732. In response to absence of matching phase and frequency of the signals received at its first and second inputs 730, 732, the phase match detector 710 produces a first DC voltage value indicative of absence of a match. In response to matching phase and frequency of the signals received at its first and second inputs 730, 732, the phase match detector 710 produces a second DC voltage value indicative of a match.

In some embodiments, the phase match detector 710 includes a synchronous detector. In some embodiments, the synchronous detector includes an analog multiplication circuit that multiplies the signals at the first and second detector inputs 730, 732 to produce the control signal at the detector output 512 that is indicative of whether the multiplied signals have matching phases and matching frequencies. Alternately, this could be determined by calculating the root-mean-square (RMS) value of each signal, and multiplying these together and then by the cosine of the phase difference between the two waveforms. The average product of the two waveforms ranges from 1 to 0 as the phase difference between the two signals ranges between 0 (purely resistive) e.g., during potential aberrant ESI current flow when $Z_B$ is coupled in parallel, and −90 or 90 degrees (purely reactive) e.g., during normal ESI current flow when $Z_B$ is not coupled in parallel.

Referring to FIGS. 7-8, assuming that the phase match detector 710 includes a synchronous detector, during the first time interval, t0 to t1, an AC voltage signal provided at the first input 730 of the phase match detector 710 is phase shifted relative to phase of the AC reference signal provided at the second input node 732 of the phase match detector 710 detector 710. During the first time interval, the virtual switch 510 is in an open state, the body impedance $Z_B$ is not coupled in parallel with the protective impedance $Z_P$, and there is no aberrant ESI current flow. During the first time interval, a phase shift is imparted to the reflected AC reference frequency signal by reactive elements (not shown) within the protective impedance $Z_P$. Tus, AC voltage signal at the first input 730 of the phase match detector 710 detector 710 is phase shifted relative to the AC reference signal at the second input node 732 of the phase match detector 710 detector 710 As a result, during the first time interval t0 to t1, the phase match detector 710 detector 710 produces a DC control signal voltage on output line 512 having the first value indicative of absence of a phase and frequency match between the reflected AC frequency signal and the reference AC frequency signal, which is indicative of the absence of $Z_B$ coupling between the first and second nodes $N_1$, $N_2$.

During the second time interval, t1 to t2, an AC voltage signal provided at the first input 730 of the phase match detector 710 detector 710 is in phase (i.e. not phase shifted) with the reference AC signal provided at the second input 732 of the phase match detector 710 detector 710. During the second time interval, the virtual switch 510 is in a closed state, the body impedance $Z_B$ is coupled in parallel with the protective impedance $Z_P$, and there is aberrant ESI current flow. During the second time interval, has a different phase shift is imparted to the reflected AC frequency signal since the patient's body tissue 204 impedance $Z_B$, which is coupled in parallel with protective impedance $Z_P$, is generally resistive, not reactive, and therefore, results in the imparting of a different phase shift to the reflected AC reference frequency signal. Thus, during the second time interval t1 to t2, the phase match detector 710 detector 710 produces a DC control signal voltage on output line 512 having the first value indicative of a matched phase and frequency between the reflected AC frequency signal and the reference AC frequency signal, which is indicative of the presence of $Z_B$ coupled between the first and second nodes $N_1$, $N_2$.

It will be understood that the second monitor circuit 504 may operate independent of whether the electrosurgical signal generator 502 is operating to produce an ESI signal. Thus, even with the electrosurgical signal generator 702 turned off, the second monitor circuit 504 can operate to determine whether an aberrant ESI signal path exists. Moreover, during normal operation of the electrosurgical signal generator 502, some portion of an ESI return signal that flows through the patient return pad 210 may be coupled from secondary winding 714 to the primary winding 712. However, the phase and frequency of the ESI return signal do not match those of the AC reference frequency signal, and therefore, the coupling of an ESI frequency signal to the s phase match detector 710 does not cause false detection results. produces an output control signal at line 512 indicating no match. Moreover, the first and second capacitors and resistors C1, R1 and C2, R2 act to filter out the higher frequency ESI signal components that otherwise may be coupled from the secondary winding 714. Thus, the presence of an ESI signal does not impact performance of the second monitor circuit.

The above description is presented to enable any person skilled in the art to create and use an electrosurgical system with patient protection against injury due to insulator damage. Various modifications to the embodiments will be clear to those skilled in the art, and the generic principles defined herein may be applied to other embodiments and applications without departing from the spirit and scope of the invention. In the preceding description, numerous details are set forth for explanation. However, one of ordinary skill in the art will realize that the circuitry might be practiced without the use of these specific details. In other instances, well-known circuits and processes are shown in block diagram form in order not to obscure the description of the invention with unnecessary detail. Identical reference numerals may be used to represent different views of the same or similar item in different drawings and in the specification. Tus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

What is claimed is:

1. An apparatus to detect electrical contact between an anatomical tissue portion near a surgical site and a protective shield conductor surrounding an active conductor of an electrosurgical instrument comprising:
   a transformer including a primary winding and a secondary winding;
   an alternating current (AC) reference frequency signal generator coupled to inject an AC reference frequency signal to the primary winding;
   a first reactive impedance coupled in parallel with the secondary winding between a first node and a second node;
   wherein the primary and secondary windings are magnetically coupled such that the injected AC reference frequency signal in the primary winding induces an AC reference frequency signal in the secondary winding and the secondary winding is configured to reflect back to the primary winding a reflected AC reference frequency signal having a phase shift relative to the injected AC reference frequency signal that is indicative of an impedance between the first and second nodes; and
   a phase match detector circuit is configured to detect a phase match between the AC reference frequency signal and the reflected AC reference frequency signal.

2. The apparatus of claim 1, further comprising:
   a patient contact pad to electrically contact a second anatomical tissue portion apart from the surgical site; and
   a first conductor path to couple the reactive impedance to the protective shield conductor and a second conductor path to couple the reactive impedance to the patient contact pad.

3. The apparatus of claim 1,
   wherein the phase match detector circuit includes a synchronous detector.

4. The apparatus of claim 1,
   wherein the phase match detector circuit includes a synchronous detector; and
   wherein the synchronous detector includes a multiplier circuit.

5. The apparatus of claim 1 further including:
   wherein the reflected AC reference frequency signal includes a reflected AC reference frequency current signal; further including:
   a converter circuit coupled to convert the reflected AC reference frequency current signal to an AC reference frequency voltage signal and to provide the converted signal to the phase match detector circuit.

6. The apparatus of claim 1,
   wherein the reflected AC reference frequency signal includes a reflected AC reference frequency current signal; further including:
   an amplifier circuit coupled to produce an AC reference frequency voltage signal based upon the reflected reference frequency current signal.

7. The apparatus of claim 1,
   wherein the reflected AC reference frequency signal includes a reflected reference frequency current signal; further including:
   a resistor coupled between a first end of the secondary winding and to a reference voltage; and
   an amplifier circuit coupled to produce a reference frequency voltage signal based upon a voltage across the resistor.

8. The apparatus of claim 1,
   wherein the reactive impedance is coupled between a first end of the secondary winding and the first node; and
   wherein the reactive impedance is coupled between a second end of the secondary winding.

9. The apparatus of claim 1 further including:
   a first electrical path coupled between the first node and the protective shield conductor; and
   a second electrical path coupled between a patient contact pad and the second node.

10. The apparatus of claim 1 further including:
    a first electrical conductor path coupled between the first node and the protective shield conductor to couple to the first node, the anatomical tissue portion in electrical contact with the protective shield conductor;
    a patient contact pad to electrically contact a second anatomical tissue portion; and
    a second electrical conductor path coupled between the patient contact pad and the second node.

11. The apparatus of claim 1 further including:
    a first electrical conductor path coupled between the first node and the protective shield conductor to couple to the first node, the anatomical tissue portion in electrical contact with the protective shield conductor;
    a patient contact pad to electrically contact a second anatomical tissue portion; and
    a second electrical conductor path coupled between the patient contact pad and the second node.

12. A method to protect a patient from injury due to electrical contact between an anatomical tissue portion and a protective shield conductor surrounding an active conductor of an electrosurgical instrument comprising:
    coupling a reactive impedance between the protective shield conductor and a patient contact pad;
    coupling the reactive impedance in parallel with a secondary winding of a transformer circuit;
    using an electrosurgical signal generator to provide an electrosurgical signal to the active conductor of the electrosurgical instrument;
    using an AC reference signal generator to generate an AC reference frequency signal;
    injecting the AC reference frequency signal to a primary winding of the transformer circuit; and
    detecting whether a reflected AC reference frequency signal in the secondary winding of the transformer circuit matches phase of the AC reference frequency signal injected to the primary winding of the transformer circuit.

13. The method of claim 12 further including:
    coupling the reactive impedance between the protective shield conductor and a patient contact pad.

14. The method of claim 12 further including:
    coupling the reactive impedance between the protective shield conductor and a patient contact pad; and
    electrically contacting a second anatomical tissue portion to the patient contact pad.

15. The method of claim 12 further including:
    halting the electrosurgical signal on the active conductor in response to detection of a phase match between the reflected AC reference frequency signal in the secondary winding of the transformer circuit and the injected AC reference frequency signal.

16. The method of claim 12 further including:
coupling the reactive impedance between the protective shield conductor and a patient contact pad;
electrically contacting an anatomical tissue portion to the patient contact pad; and
halting the electrosurgical signal on the active conductor in response to detection of a phase match between the reflected AC reference frequency signal in the secondary winding of the transformer circuit and the injected AC reference frequency signal.

17. An apparatus to detect electrical contact between an anatomical tissue portion near a surgical site and a protective shield conductor surrounding an active conductor of an electrosurgical instrument comprising:
a transformer including a primary winding and a secondary winding;
means for injecting an AC reference frequency signal to the primary winding;
a first reactive impedance coupled in parallel with the secondary winding between a first node and a second node;
wherein the primary and secondary windings are magnetically coupled,
such that the AC reference frequency signal injected to the primary winding induces an AC reference frequency signal in the secondary winding that flows through the first reactive impedance, and
such that the secondary winding reflects back to the primary winding a reflected AC reference frequency signal having a phase shift relative to the injected AC reference frequency signal that is indicative of an impedance between the first and second nodes; and
means for detecting a phase match between the AC reference frequency signal and the reflected AC reference frequency signal.

18. The apparatus of claim 17, further comprising:
patient contact pad to electrically contact a second anatomical tissue portion apart from the surgical site; and
a first conductor path to couple the reactive impedance between the protective shield conductor and a second conductor path to couple the reactive impedance to the patient contact pad.

* * * * *